(12) United States Patent
Tatarczyk et al.

(10) Patent No.: US 7,656,530 B2
(45) Date of Patent: Feb. 2, 2010

(54) COLOR DENSITY MEASURING DEVICE

(75) Inventors: Christina Tatarczyk, Groebenzell (DE); Joachim Tatarczyk, Groebenzell (DE)

(73) Assignee: Theta System Elektronik GmbH (DE)

( * ) Notice: Subject to any disclaimer, the term of this patent is extended or adjusted under 35 U.S.C. 154(b) by 159 days.

(21) Appl. No.: 11/525,485

(22) Filed: Sep. 22, 2006

(65) Prior Publication Data

US 2007/0064234 A1 Mar. 22, 2007

(30) Foreign Application Priority Data

Sep. 22, 2005 (DE) ........................ 10 2005 045 357

(51) Int. Cl.
*G01N 21/25* (2006.01)

(52) U.S. Cl. ...................... 356/407; 356/420

(58) Field of Classification Search ......... 356/402–425; 358/515–521; 250/226
See application file for complete search history.

(56) References Cited

U.S. PATENT DOCUMENTS

| 5,751,429 | A | 5/1998 | Wada et al. |
| 5,856,876 | A | 1/1999 | Sasanuma et al. |
| 6,722,281 | B2 * | 4/2004 | Yamamoto ................... 101/484 |
| 6,842,250 | B2 | 1/2005 | Schwarz |
| 2003/0142314 | A1 * | 7/2003 | Hubble et al. ................ 356/402 |
| 2005/0133693 | A1 * | 6/2005 | Fouquet et al. ........... 250/214 R |

FOREIGN PATENT DOCUMENTS

EP  1 260 877  11/2002

* cited by examiner

*Primary Examiner*—Gregory J Toatley, Jr.
*Assistant Examiner*—Tri T Ton
(74) *Attorney, Agent, or Firm*—Gerald E. Hespos; Anthony J. Casella

(57) ABSTRACT

A color density measuring device (10) for determining the color density of an ink layer applied to a printing material (22), having a light source (24) for illuminating the printing material (22) and a sensor for receiving the light remitted from the printing material (22), is characterized according to the invention in that the sensor is fashioned as a multicolor image sensor (12), and a device (14, 24, 26; 30) is provided with the aid of which the light incident at the multicolor image sensor (12) is restricted to at least one predetermined wavelength band.

16 Claims, 4 Drawing Sheets

COLOR DENSITY MEASURING DEVICE

BACKGROUND OF THE INVENTION

1. Field of the Invention

The invention relates to a color density measuring device for determining the color density of an ink layer applied to a printing material or subject, the color density measuring device having a light source for illuminating the printing material, and a sensor for receiving the light remitted from the printing material. The invention further relates to the use of such a color density measuring device on a printing apparatus for multicolor printing. Moreover, the invention also relates to a method for determining the color density of at least one of the three colors cyan, magenta or yellow, or black on a colored material.

2. Description of the Related Art

Particularly for the purpose of controlling the ink management in the case of printing units for multicolor printing, it is customary to determine the color density of an ink layer applied to the printing material. So-called reflected colored light densitometers are currently used for this purpose. This type of measurement is based on a linearity between a printed quantity of ink and optical density. The density measurement is performed using the known principle of remission measurement of body colors. An emitted measuring light beam penetrates the ink layer and is reflected at the interface between ink layer and printing material. The reflected light penetrates the ink layer once again and is received by a photoelement of the reflected colored light densitometer. Upon two-fold penetration of the ink layer, the originally white measuring light is colored and attenuated by absorption. The remission of the light is reduced in a typical wavelength region. An electric signal proportional to the light intensity is generated at the photoelement. This electric signal contains the information, resulting from the modulated reflected light, relating to type and quantity of the printed color that is used to determine the density value.

Densitometers having so-called status filters or color filters are known which can be used for separately detecting the printing inks cyan, magenta, yellow and also black. In the case of these densitometers, individual photoelements for white light are arranged downstream of a total of four individual filters each having different transmission ranges. The photocells form individual measuring channels for each of the printing inks cyan, magenta and yellow. The density of these colored inks is determined in each case in the low remission range because variations in remission take place here that are prominent and can be effectively measured. The density of cyan is therefore measured with the aid of a red filter at a wavelength of approximately 600 nm. Similarly, magenta is measured with a green filter at approximately 530 nm, and yellow is measured with a blue filter at approximately 430 nm.

The characteristic of the filters is laid down in the standards DIN 16 536-2 and ISO 5-3. Filters of status DIN E are used in Europe. With regard to the SWOP color standard, ISO T filters are customary in the USA and, to some extent, in England.

This procedure is illustrated in FIG. 1 using the example of remission curves of cyan for various color densities. The density is measured with the aid of a red filter (transmission range at a wavelength of approximately 600 nm) in the region of the largest variations.

It is an object of the invention to specify a color density measuring device for determining the color density and the use thereof, as well as a method for determining the color density which together lead to a substantial reduction in cost by comparison with known measuring devices and methods.

SUMMARY OF THE INVENTION

The invention provides for the sensor of a color density measuring device to be fashioned as a multicolor image sensor that is directed to the printing material. Furthermore, the invention provides a device with the aid of which the light incident at the multicolor image sensor is restricted to at least one predetermined wavelength band. In the case of the inventive method for determining the color density of at least one of the colors cyan, magenta or yellow on a colored material, this material is illuminated with light and a pictorial recording of the light remitted by the material is produced with the aid of a multicolor image sensor. The light incident at the multicolor image sensor is restricted to at least one predetermined wavelength band. According to the invention, the color density is determined by evaluating the pictorial recording produced with the aid of the multicolor image sensor by taking account of the determined light intensity at at least one of the pixels of the multicolor image sensor.

The inventive multicolor image sensor is understood as a sensor that is sensitive to light and has a multiplicity of individual sensor points for these different colors, in particular for the colors red, green and blue. The individual sensor points in this case have a different relative spectral sensitivity. In particular, the sensitivity to blue light has a maximum at a wavelength of approximately 460 nm, the sensitivity to green light has a maximum at a wavelength of approximately 520 to 530 nm, and the sensitivity of the sensor points to red light has a maximum at approximately 620 to 640 nm. Such image sensors can be bought at particular cost advantage because, for example, they are currently already being applied in comparatively high numbers of items for CCD cameras. It is therefore particularly preferred in accordance with the invention to form the multicolor image sensor with a customary multicolor camera, in particular a red, green, blue camera.

The invention renders it possible to operate in the case of a color density measurement with a particularly cost-effective multicolor image sensor that, on the basis of the multiplicity of pixels or sensor points provided on it, also delivers a multiplicity of individual measuring points for the individual color density measurement. According to the invention, the light respectively incident at the individual sensor points of the multicolor image sensor is restricted in this case to at least one predetermined wavelength band. This restriction is preferably performed by means of a filter device that is, in particular, inserted in the beam path of the emitted light upstream of the multicolor image sensor. Consequently, only a subregion of their wavelength spectra is led through the provided filter device to the individual pixels of the multicolor image sensor. Thus, for example, the individual red sensor point provided for red light receives only that subregion of the wavelength spectrum for red light which is required for a color density measurement in the case of a cyan remission curve.

The remaining sensor points of the multicolor image sensor can be used, if appropriate, to measure the color balance and secondary densities.

It is possible, in particular by selective provision of filter devices having various transmission ranges, to address the individual sensor points of the multicolor image sensor with corresponding subregions of the associated wavelength spectra in such a way that color density measurements of yellow and/or magenta are also possible in a way similar to the color density measurement of cyan that has been explained.

Particularly advantageous to this end is a restriction in a preferred form of a filter device having at least one second transmission range with the aid of which the incident light is restricted to a subregion of the wavelength spectrum of a second color of the colors of the multicolor image sensor, in particular of the three colors red, green or blue.

Furthermore, the restricting device also particularly advantageously has a third transmission range with the aid of which the incident light is restricted to a subregion of the wavelength spectrum of a third color of the multicolor image sensor, in particular of the three colors red, green or blue.

It is possible with the aid of such devices and, in particular, filter devices to make simultaneous color density measurements of at least and, in particular, three different colors, in the present case the colored inks cyan, magenta and yellow, doing so simultaneously and in the course of a pictorial recording that is also relatively large. The individual sensor points for red, green and blue light are respectively allocated a subregion of the associated wavelength spectrum with the aid of the filter device. In contrast, the transmission ranges of the filter device that do not match the sensitivity range of the individual sensor points pass light from the wavelength regions to which these "non-matching" sensor points are not sensitive, or are scarcely so.

The above-named subregions, in particular the transmission ranges of the filter device should be restricted with particular advantage to a region between approximately 420 nm and approximately 460 nm, in particular between 430 nm and approximately 450 nm. With the aid of such a transmission range, the sensitivity of a sensor point that is sensitive to blue light can be restricted in such a way that said sensor point acts as a density measuring device or densitometer for the colored ink yellow.

A further advantageous subregion of the light restricted according to the invention is the region between approximately 510 nm and approximately 550 nm, in particular between approximately 520 nm and approximately 540 nm. With the aid of such a subregion, the sensitivity of a sensor point that is sensitive to green light can be restricted to a wavelength region such that said point acts as density measuring device for the colored ink magenta.

Finally, a third advantageous subregion to be recommended is that between approximately 610 nm and approximately 650 nm, in particular between approximately 620 nm and approximately 640 nm. With the aid of this subregion, the sensitivity of a sensor point that is fundamentally sensitive to red light can be restricted to a wavelength region such that said sensor point acts, just as explained using the example in the introduction, as a density measuring device for the colored ink cyan.

Alternatively or in addition to these subregions, it is preferred according to the invention to provide a device with the aid of which the light incident at the multicolor image sensor is restricted to a subregion of the wavelength spectrum of infrared light. This development is based on the finding that colored printing inks are transparent to infrared light, whereas the black printing inks based on carbon remit infrared light. Furthermore, the pixels of multicolor image sensors are also sensitive in the infrared region. Consequently, by restricting the incident light to infrared light as provided by the invention it is possible also to determine the density of the printing ink black independently of the colored inks virtually without additional outlay. It is particularly advantageous in this case that this measurement can even be made over a large range of image and/or subject because of the pictorial recording according to the invention.

In order to be able to provide the above-named transmission ranges in a single filter device in a cost-effective fashion, the invention preferably provides for the use of a multiple bandpass filter for this purpose, in particular a so-called triple filter such as is customarily used for multifluorescence measurements. Such multiple bandpass filters can also be produced very cost-effectively.

In addition to a restriction of the light incident on the multicolor image sensor by means of filtering, it is also possible alternatively or in addition already to restrict the wavelength of the light emanating from the light source to one or more predetermined wavelength bands. Such an illumination restricted to specific wavelength bands can be provided particularly advantageously by means of a number of light emitting diodes or lasers.

As has been mentioned, color density measurements can be made in a pictorial recording with the aid of the color density measuring device according to the invention, the use thereof and the method according to the invention. During the recording, the individual sensor points or pixels of the multicolor image sensor used according to the invention can respectively serve to make individual measurements at various image regions within the pictorial recording. The interrelationships between these individual measurements can then be found, this being done according to the invention with the aid of appropriate evaluation software. Furthermore, it is possible according to the invention to carry out a measurement simultaneously for all three primary colors cyan, magenta and yellow. The time outlay required for the measurements is thereby substantially lowered. However, the time outlay is also reduced because a need otherwise arising to move the image sensor to a number of measuring ranges can be omitted owing to the comparatively large pictorial recording.

Furthermore, the pictorial recording according to the invention enables a comparison to be undertaken between a colored surface and a white one. Imaging need be done in this case only at an image region where such a colored image section and also a white image section are present. It is then also possible, for example, to assess the quality of the printing paper itself with the aid of the measurement at the white image section.

BRIEF DESCRIPTION OF THE DRAWINGS

Exemplary embodiments of an inventive color density measuring device are explained below in more detail with the aid of the attached schematics, in which.

DETAILED DESCRIPTION OF THE PREFERRED EMBODIMENTS

Figure 1:
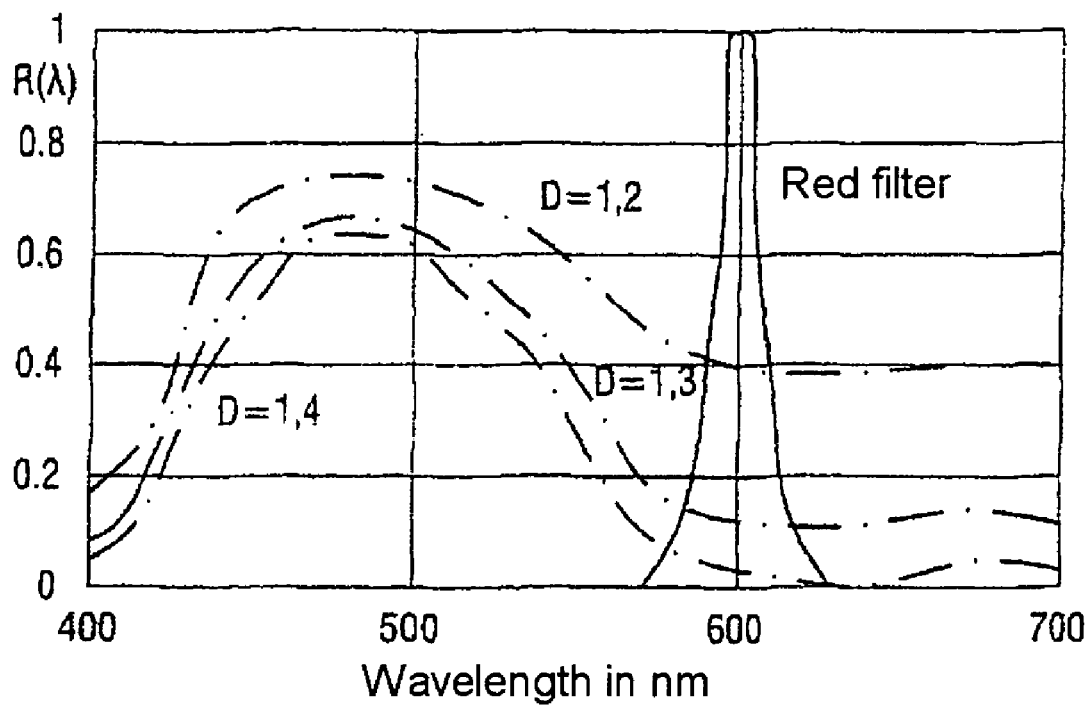
FIG. 1 shows a graph of remission curves of cyan for various color densities, and the associated density measurement with the aid of a red filter.
Figure 2:
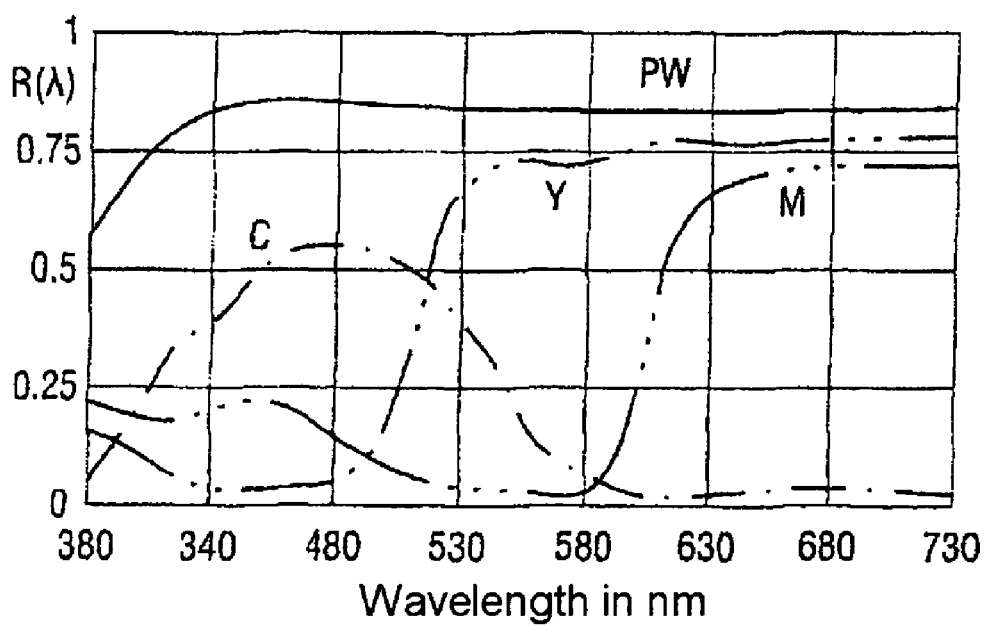
FIG. 2 shows a graph of the spectral remission curves of the colored inks cyan, magenta and yellow and of the unprinted white paper.

The spectral remission curves of the printing inks cyan (C), magenta (M) and yellow (Y) and of an unprinted white paper (PW) are illustrated graphically in FIG. 2. The curves show for white paper a virtually uniformly high remission of above approximately 0.8 in the entire wavelength region above approximately 430 nm. By contrast therewith, the spectral remission curves of the colored inks cyan, magenta or yellow exhibit rising, and also falling, sections over the illustrated wavelength region. In order respectively to provide density measurements with a high information content in the case of the remission of printing inks that is illustrated in such a way, as already mentioned at the beginning the density measurements are respectively undertaken in the low remission range of the colored inks. The measurements are therefore made specifically in comparatively restricted wavelength regions of the spectral remission curves. As illustrated in FIG. 1, in the case of customary density measurements, an individual red filter is inserted upstream of a photoelement sensitive to white light and in each case filters out from the remission curves of cyan only a wavelength section around approximately 600 nm for the photoelement. Depending on color density, correspondingly strong deviations result in light intensity for the photoelement.

Figure 3:
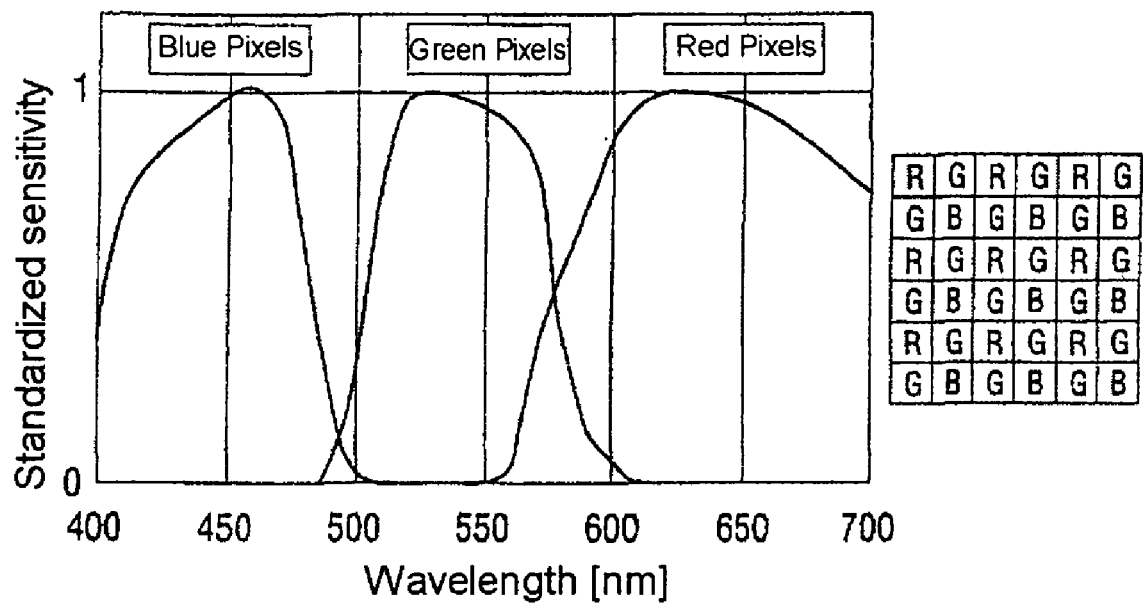
FIG. 3 shows a graph of the typical standardized sensitivity of a multicolor camera, a red, green blue camera in the present case.

According to the invention, by contrast, the use of a customary multicolor camera, in particular a red, green, blue camera is proposed which comprises on a flat image sensor a multiplicity of sensor points for different colors, in this case a multiplicity of blue, green and red sensor points or pixels. A diagram in the right-hand area of FIG. 3 shows the two-dimensional arrangement of such blue (B), green (G) and red (R) pixels or sensor points on such a color camera. Furthermore, the left-hand area of FIG. 3 illustrates the typical sensitivity of the individual pixels with the aid of their standardized sensitivity.

It is clearly to be seen from FIG. 3 that the blue pixels have a sensitivity maximum at approximately 460 nm, the green pixels have a sensitivity maximum at approximately 520 nm to 540 nm, and the red pixels have a sensitivity maximum at approximately 620 to 630 nm. The pixels of such type are preferably produced from silicon and therefore act as individual photosensitive elements whose sensor signal can correspondingly also be evaluated individually.

Inserted upstream of the multicolor camera of such sensitivity is a filter device that is fashioned as a multiple bandpass filter, in particular as a triple bandpass filter or a so-called triple filter. Such a filter device has three respectively restricted transmission ranges. With as high a relative transmission as possible (ideally approximately 1), a first transmission range is restricted to a wavelength region between approximately 430 nm and approximately 450 nm. With as high a relative transmission as possible (ideally approximately 1), a second transmission range is restricted to the wavelength section between approximately 520 nm and approximately 540 nm. Finally, with as high a relative transmission as possible (ideally approximately 1), the third transmission range comprises only the wavelength region between approximately 620 nm and approximately 640 nm.

The color density measuring device 10 fashioned in such a way is illustrated in FIG. 5 once again with its camera 12 acting as multicolor image sensor, as well as the upstream triple filter 14 acting as filter device.

During operation, the color density measuring device 10 is directed, for example inside a further printing apparatus (not illustrated) for multicolor printing, onto a printing material 22 that is provided with an ink layer and is, therefore, colored.

The color density measuring device 10 is, moreover, coupled operationally to a control and evaluation circuit 18 via lines 16. Furthermore, the color density measuring device 10 is supported such that it can be displaced on a cross member 20 by a motor.

The multicolor camera 12 arranged in such a way is then used not, for example, to take customary color photographs, but color density measurements are carried out that have at least the same measurement quality as do measurements with the aid of customary densitometers.

Figure 4:
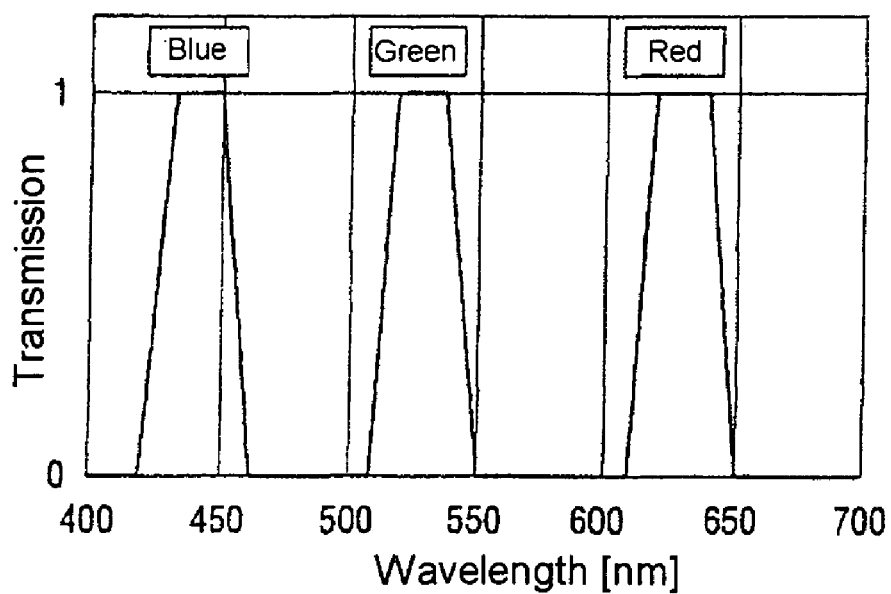
FIG. 4 shows a graph of the transmission of an inventive triple bandpass filter.
Figure 6:
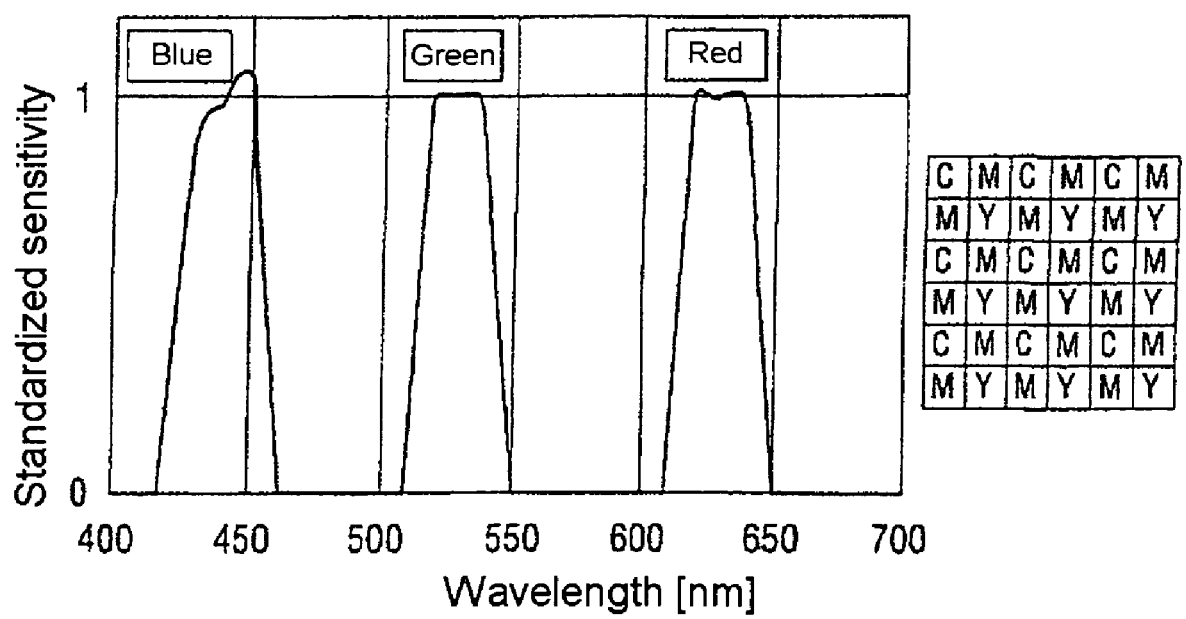
FIG. 6 shows a graph of the standardized sensitivity of the multicolor camera used according to the invention, together with the triple bandpass filter according to the invention.

Such color density measurements are possible because a particular standardized sensitivity of the individual pixels of the multicolor camera 12 results (see left-hand area of FIG. 6) over the entire wavelength region owing to the inventive combination of the triple bandpass filter 14 (see FIG. 4) with a multicolor camera 12 (see FIG. 3). A high standardized sensitivity thus remains for the blue pixel only in the wavelength region between approximately 430 nm and approximately 450 nm. For the green pixel, a high standardized sensitivity is restricted to the wavelength region between approximately 520 nm and 540 nm. The red pixel is particularly sensitive only in the wavelength region between approximately 620 nm and approximately 640 nm.

If this sensitivity resulting in the case of the multicolor camera 12 provided with the triple bandpass filter 14 (see left-hand area of FIG. 6) is covered with spectral remission curves of the colored inks cyan, magenta and yellow as well as of the unprinted white paper (see FIG. 2), it is to be seen that a densitometer for cyan (C) has been provided with the aid of the filtered "red" pixel (cf. also FIG. 1), a densitometer has been provided for magenta (M) with the aid of the "green" pixel, and a densitometer has been provided for yellow (Y) with the aid of the "blue" pixel. This functionality of the multicolor camera 12 used in accordance with the invention is illustrated once more in the right-hand area of FIG. 6 with the sensor points correspondingly designated (see, in particular, by comparison with the right-hand area of FIG. 3).

It is therefore possible to use the color density measuring device 10 to undertake a total of three density measurements in only a single recording and, furthermore, to carry out a comparison with an unprinted white paper surface, if appropriate.

Figure 5:
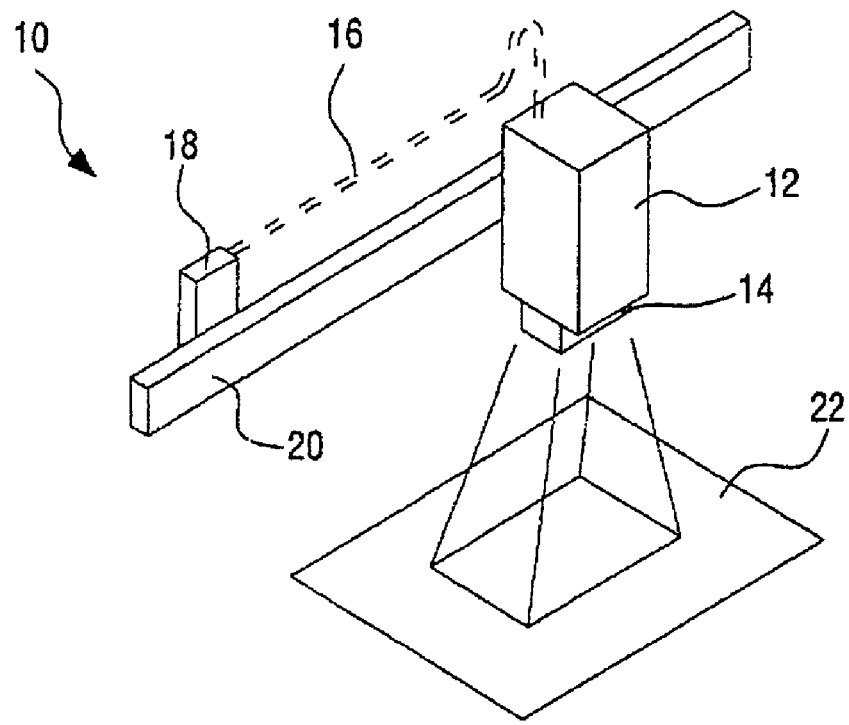
FIG. 5 shows a greatly simplified perspective view of a first exemplary embodiment of an inventive color density measuring device.
Figure 7:
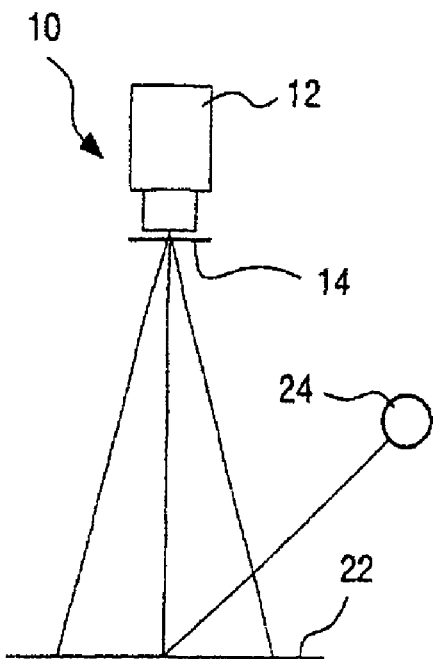
FIG. 7 shows a greatly simplified side view of a second exemplary embodiment of an inventive color density measuring device.

A second exemplary embodiment of a color density measuring device 10 is illustrated in FIG. 7; it is fashioned like the example illustrated in FIG. 5 with regard to the multicolor camera 12, the triple bandpass filter 14 and the printing material 22. In the exemplary embodiment in accordance with FIG. 7, however, the multicolor camera 12 cannot be moved, but is fastened on a stand (not illustrated) in a stationary fashion. A light source 24 in the form of a luminaire emitting light over the entire visible wavelength spectrum is, moreover, provided on the color density measuring device 10 in accordance with FIG. 7. This luminaire is arranged at a principal irradiation angle of approximately 45° to the plane of the printing material 22. In the case of the exemplary embodiment in accordance with FIG. 7, the triple bandpass filter 14 is likewise inserted into the beam path of the light remitted by the printing material 22 directly upstream of a lens of the multicolor camera 12.

Figure 8:
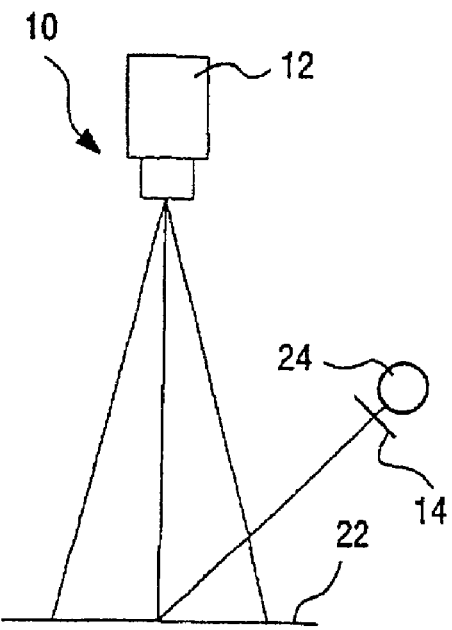
FIG. 8 shows a greatly simplified side view of a third exemplary embodiment of an inventive color density measuring device.

FIG. 8 shows an exemplary embodiment of a color density measuring device 10 in which the triple bandpass filter 14 is inserted not upstream of the multicolor camera 12, but is inserted, directly downstream of the light source 24, into the beam path of the light emitted by the light source 24. Such an arrangement of the triple bandpass filter 14 already restricts the light directed onto the printing material 22 to the desired wavelength bands named above.

Figure 9:
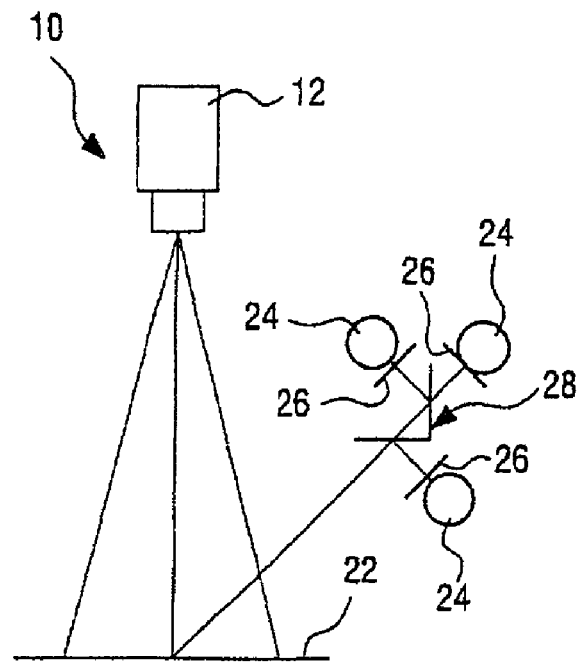
FIG. 9 shows a greatly simplified side view of a fourth exemplary embodiment of an inventive color density measuring device.

FIG. 9 illustrates an exemplary embodiment in which instead of a single light source 24 and a triple bandpass filter 14 a total of three light sources 24 are provided upstream of which a single bandpass filter 26 is inserted in each case. Furthermore, the illumination means of such a type are assigned a light mixing system 28 in the form of color interference filters, said light mixing system being used to unite the beam paths of the three light sources 24 to form one beam path.

Figure 10:
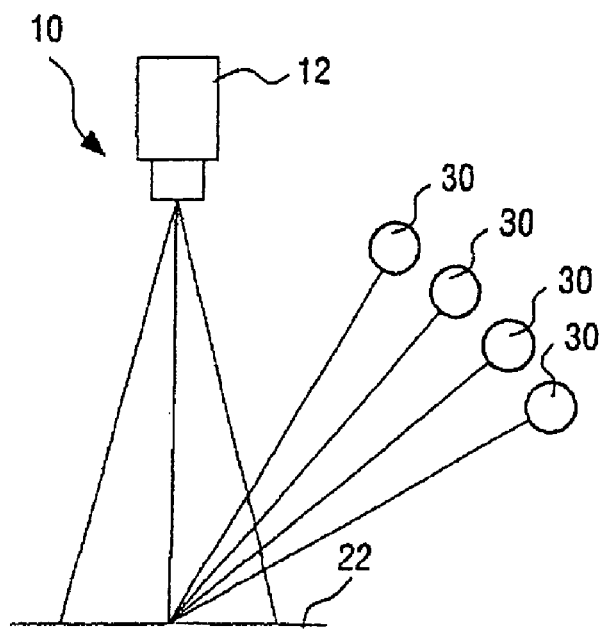
FIG. 10 shows a greatly simplified side view of a fifth exemplary embodiment of an inventive color density measuring device.

Finally, FIG. 10 illustrates an exemplary embodiment in which a total of four light sources 30 are provided. These light sources 30 are arranged next to one another and directed individually in each case onto the printing material 22, a principal irradiation angle of approximately 45° to the plane of the printing material again being observed in each case (by contrast with the illustration, which is purely schematic). Of these four light sources 30, three are fashioned as light emitting diodes or laser luminaries with specific wavelength spectra, restricted in accordance with the invention, in the region of blue, green and red light. The fourth light source 30 is an infrared luminaire and its wavelength band is likewise restricted. As explained above, this light source 30 from the infrared region can then be used in cooperation with the multicolor camera 12 to measure the density of the printing ink black.

What is claimed is:

1. A color density measuring device for determining the color density of an ink layer applied to a printing material, having a light source for illuminating the printing material and a sensor for receiving the light remitted from the printing material, characterized in that the sensor is fashioned as a multicolor image sensor formed with a multicolor camera having a multiplicity of individual red, blue and green sensor points, wherein each of the sensor points has a corresponding wavelength spectrum for the specific color, and a device is provided with the aid of which the light incident at the multicolor image sensor is restricted to at least one predetermined wavelength band and which includes a triple bandpass filter device having three respectively restricted transmission ranges wherein each of the three respectively restricted transmission ranges is restricted to a subregion of the wavelength spectrum of the individual red, blue and green sensor points in such a way that regions of the wavelength spectrum outside of the subregion for the specific color are not passed through the filter device, wherein the subregion of the wavelength spectrum for each of the specific colors lies within a maximum spectral sensitivity of the corresponding sensor point.

2. The color density measuring device of claim 1, characterized in that a first transmission range of the three respectively restricted transmission ranges is restricted to a subregion between approximately 510 nm and approximately 550 nm, in particular between approximately 520 nm and approximately 540 nm.

3. The color density measuring device of claim 2, characterized in that a second transmission range of the three respectively restricted transmission ranges is restricted to a subregion between approximately 420 nm and approximately 460 nm, in particular between approximately 430 nm and approximately 450 nm.

4. The color density measuring device of claim 3, characterized in that a third transmission range of the three respectively restricted transmission ranges is restricted to a subregion between approximately 610 nm and approximately 650 nm, in particular between approximately 620 nm and approximately 640 nm.

5. The color density measuring device of claim 1, characterized in that the light incident at the multicolor image sensor is restricted with the aid of the device to a subregion of the wavelength spectrum of infrared light.

6. The color density measuring device of claim 1, characterized in that the filter device is upstream of the multicolor image sensor.

7. The color density measuring device of claim 1, characterized in that the filter device is downstream of the light source.

8. The color density measuring device of claim 1, characterized in that a number of light sources are provided, preferably in each case with an associated downstream filter device.

9. A method for determining the color density of at least one of the colors cyan, magenta or yellow on a colored material, characterized by the steps of:
    illuminating the material with light,
    producing a pictorial recording of the light remitted by the material with the aid of a multicolor image sensor having a multiplicity of individual red, blue and green sensor points, wherein each of the sensor points has a corresponding wavelength spectrum for the specific color,
    restricting the light incident at the multicolor image sensor to three transmission ranges with the aid of a triple bandpass filter, wherein each of the three transmission ranges is restricted to a subregion of the wavelength spectrum of the individual red, blue and green sensor points in such a way that regions of the wavelength spectrum outside of the subregion for the specific color are not passed wherein the subregion of the wavelength spectrum for each of the specific colors lies within a maximum spectral sensitivity of the corresponding sensor point, and
    evaluating the pictorial recording made with the aid of the multicolor image sensor by taking account of the determined light intensity at at least one of each of the individual red, blue and green sensor points of the multicolor image sensor.

10. The method of claim 9, characterized by the step of: producing the pictorial recording at an image region of the material in which are allocated both a colored and a white image section.

11. A color density measuring device for determining the color density of an ink layer applied to a printing material, having a light source for illuminating the printing material and a sensor for receiving the light remitted from the printing material, characterized in that the sensor is fashioned as a multicolor image sensor formed with a multicolor camera having a multiplicity of individual red, blue and green sensor points, wherein each of the sensor points has a corresponding wavelength spectrum for the specific color, and wherein the light source emits light that is restricted to three transmission ranges, wherein each of the three transmission ranges is restricted to a subregion of the wavelength spectrum of the individual red, blue and green sensor points in such a way that regions of the wavelength spectrum outside of the subregion for the specific color are not emitted, wherein the subregion of the wavelength spectrum for each of the specific colors lies within a maximum spectral sensitivity of the corresponding sensor point.

12. The color density measuring device of claim 11, wherein a first transmission range is restricted to a subregion between approximately 510 nm and approximately 550 nm, in particular between approximately 520 nm and approximately 540 nm, a second transmission range is restricted to a subregion between approximately 420 nm and approximately 460 nm, in particular between approximately 430 nm and approximately 450 nm, and a third transmission range is restricted to a subregion between approximately 610 nm and approximately 650 nm, in particular between approximately 620 nm and approximately 640 nm.

13. The color density measuring device of claim 11, further characterized in that a filter device is upstream of the multi-color image sensor.

14. The color density measuring device of claim 11, further characterized in that a filter device is downstream of the light source.

15. The color density measuring device of claim 11, further characterized in that a filter device upstream of the light source is formed with triple bandpass filter.

16. The color density measuring device of claim 11, characterized in that a number of light sources are provided, preferably in each case with an associated downstream filter device.

* * * * *